United States Patent
Olsztyn et al.

[11] Patent Number: 6,002,789
[45] Date of Patent: Dec. 14, 1999

[54] BACTERIA COLONY COUNTER AND CLASSIFIER

[75] Inventors: Paul C. Olsztyn; James H. Beyer, both of Ann Arbor; David Sullivan, Brighton, all of Mich.

[73] Assignee: Pilot Industries, Inc., Dexter, Mich.

[21] Appl. No.: 09/083,723

[22] Filed: May 22, 1998

Related U.S. Application Data

[60] Provisional application No. 60/050,605, Jun. 24, 1997.

[51] Int. Cl.$^6$ .................................................. G06K 9/00
[52] U.S. Cl. ............................. 382/133; 382/173; 435/39
[58] Field of Search ................................... 382/128, 133, 382/173, 276, 291, 323; 435/34, 39; 377/10

[56] References Cited

U.S. PATENT DOCUMENTS

| | | | |
|---|---|---|---|
| 3,720,812 | 3/1973 | Downs | 235/92 PC |
| 3,811,036 | 5/1974 | Perry | 235/92 PC |
| 3,869,083 | 3/1975 | Malmon | 235/92 PC |
| 4,353,988 | 10/1982 | Couse et al. | 435/287 |
| 4,538,227 | 8/1985 | Toraichi et al. | 364/414 |
| 4,637,053 | 1/1987 | Schalkowsky | 382/6 |
| 5,117,467 | 5/1992 | Misaki et al. | 382/6 |
| 5,403,722 | 4/1995 | Floeder et al. | 435/39 |
| 5,481,620 | 1/1996 | Vaidynathan | 382/169 |
| 5,510,246 | 4/1996 | Morgan | 435/39 |
| 5,694,478 | 12/1997 | Braier et al. | 382/133 |
| 5,744,322 | 4/1998 | Krejcarek et al. | 435/39 |

FOREIGN PATENT DOCUMENTS

| | | | |
|---|---|---|---|
| 1 174 953 | 9/1984 | Canada | C12M 1/34 |
| 60-140974 | 7/1985 | Japan | 382/323 |

OTHER PUBLICATIONS

Nobuyuki Otsu, "A Threshold Selection Method from Gray-Level Histograms," *IEEE Transactions on Systems, Man, and Cybernetics*, vol. SMC–9, No. 1, Jan. 1979; pp. 62–64.

*Primary Examiner*—Andrew W. Johns
*Attorney, Agent, or Firm*—Gifford, Krass, Groh, Sprinkle, Anderson & Citkowski, P.C.

[57] ABSTRACT

The present invention relates to a colony counter and classifier for bacterial specimens on a petri dish. The device includes a housing having a tray which accepts the petri dish containing the bacteria colonies. A line scan camera is mounted within the housing above the tray. Upon actuation, a linear motor transports the tray across the scanning line of vision for the line scan camera. Simultaneously, a fiber optic illumination system illuminates the petri dish from its side opposite the camera. As the tray is transported by the linear motor, the line scan camera successively obtains an optical image of the petri dish containing the bacteria colonies. Each line scan has a width equal to one pixel and the resulting optical images from the line scan camera are combined together to form an overall optical image of high resolution. That image is stored utilizing a digital computer. The computer then analyzes the stored optical image to both identify and count the bacteria colonies. Advanced software is also used to differentiate between single colonies and two or more colonies which abut against each other.

7 Claims, 4 Drawing Sheets

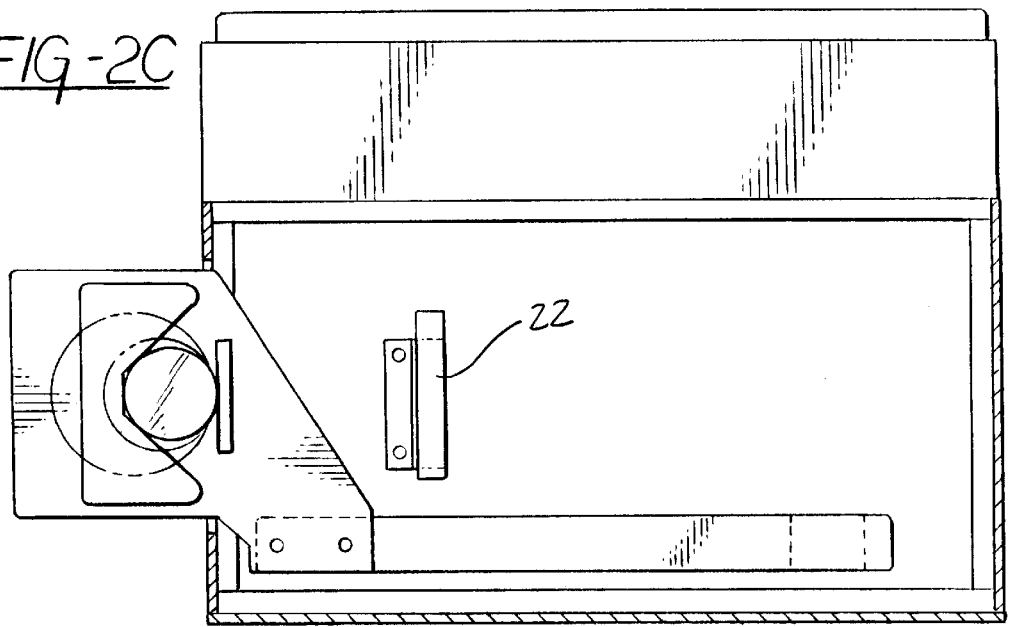
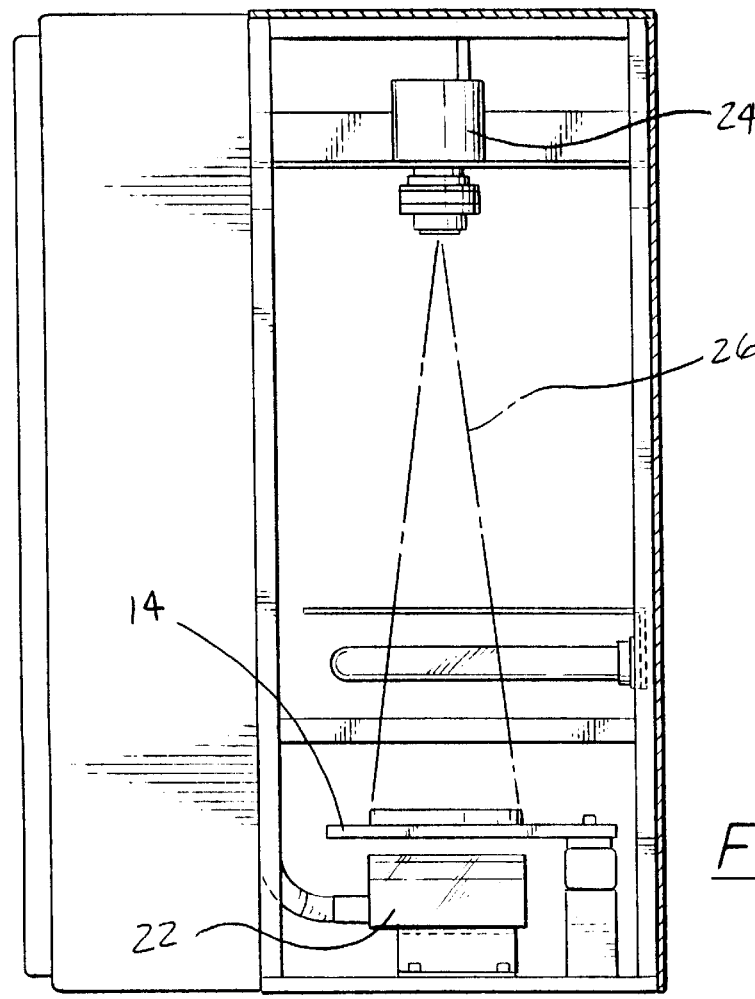

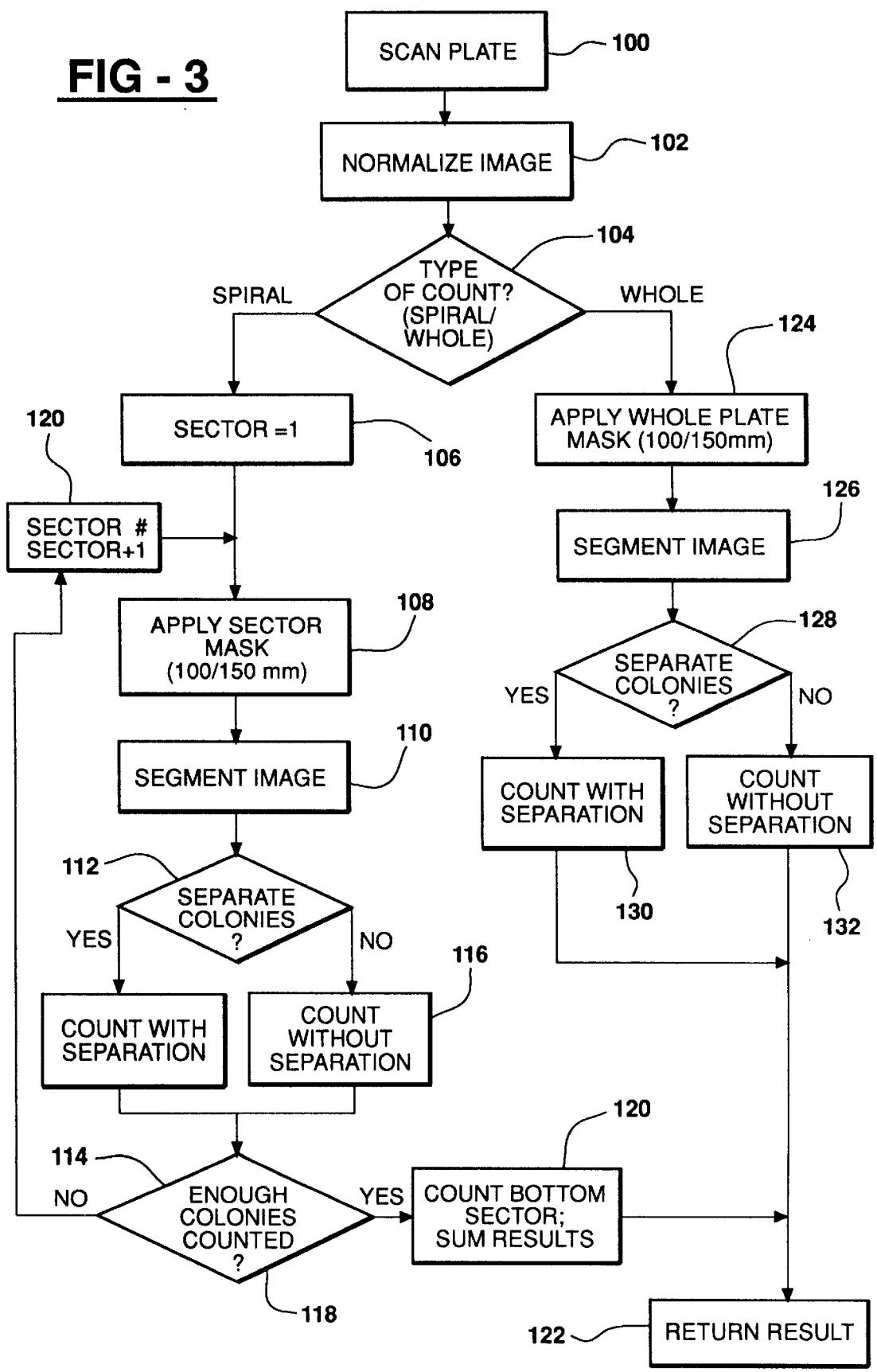

BACTERIA COLONY COUNTER AND CLASSIFIER

RELATED APPLICATION

This patent application claims priority of U.S. provisional patent application Ser. No. 60/050,605, filed Jun. 24, 1997.

BACKGROUND OF THE INVENTION

I. Field of the Invention

The present invention relates to an automated bacteria colony counter and classifier.

II. Description of the Prior Art

In order to determine the bacteria concentration in medical as well as other applications, the bacteria sample is applied to a petri dish containing gelatin. The bacteria growth forming generally circular colonies which may or may not abut against each other.

In order to determine the bacteria concentration in the specimen, after the bacteria colonies become visible, the bacteria colonies are counted. Frequently, the bacteria colonies are counted manually by a lab worker.

A primary disadvantage of manually counting the bacteria colonies in a petri dish is that it is time consuming and involves relatively high labor costs. Additionally, the manual counting of colonies by a lab worker also results in inaccurate counts of the bacteria colonies.

There have, however, been previously known devices for automatically counting bacteria colonies in a petri dish. In one previously known device, a laser beam is used to scan the petri dish and generate a digital signal as a result of that scan.

A still further disadvantage of these previously known laser scanning devices is that such devices do not perform well in certain types of gelatines, particularly in darker and more opaque gelatines.

A still further disadvantage of these previously known laser and optical devices is that they have been inadequate for accurately differentiating between single bacteria colonies and two or more bacteria colonies which abut against each other.

A still further disadvantage of these previously known laser and optical devices is that they usually require manipulation of imaging settings to obtain a good image. These systems sometimes receive manipulation of settings for each individual plate being imaged. This is a disadvantage because it means there is excessive operator intervention.

Although it would be possible to overcome some, but not all, of the disadvantages of the previously known laser scanning devices by utilizing a high resolution area scan camera, e.g. 2048 pixels times 2048 pixels, such optical cameras are very expensive to obtain and maintain.

SUMMARY OF THE PRESENT INVENTION

The present invention provides a bacteria colony counter and classifier which overcomes all of the disadvantages of the previously known devices.

In brief, the colony counter of the present invention comprises a housing having a tray for receiving the petri dish containing the colony counters. The bottom of the petri dish is illuminated by an optical fiber transmitted light source to ensure even illumination of the petri dish on the tray.

A line scanning camera is also mounted within the housing above the petri dish so that its lens is directed toward the petri dish. The line scanning camera, in the well known fashion, produces an electrical output signal representative of one line of an optical image having a width of one pixel. This output signal from the line scanning camera is connected through an appropriate A/D converter within the camera. The resulting digital signal is input to a computer via a conventional image acquisition device, or "frame grabber".

In order to form a complete optical image, a linear motor is utilized to drive the tray in a direction transverse to the optical scanning vision of the line scanning camera. Appropriate timing means are then utilized to synchronize the line scanning camera with the linear motor so that the linear motor is activated to generate a line representative of the optical image in line width equal to one pixel. Upon complete scanning of the petri dish, a complete optical image of the petri dish is stored in digital memory. Furthermore, because the line scanning camera scans the petri dish in lines having only one pixel width, high resolution, e.g. 2048 times 2048 pixels, of the petri dish are obtained. This in turn results in a resolution of about 0.075 millimeters.

After the petri dish image has been inputted into the digital computing system by the line scanning camera, a computer algorithm is then utilized to count the bacteria colonies on the petri dish. Since bacteria colonies are, by their very nature, generally circular in shape, the preferred algorithm utilizes a cone insertion method in which a cone is mathematically inserted into each colony on the stored optical image until the outer periphery of the cone reaches the outer periphery of the bacteria colony. At that time, the cross-sectional area of the cone is compared to the cross-sectional area of the optical image for that particular bacteria colony outside the cone. If this ratio is greater than a predetermined threshold, indicative that the bacteria colony is generally circular in shape, a single bacteria colony is contained in that particular area of the optical image. A bacteria colony counter is incremented and the algorithm proceeds to analyze the remaining portions of the optical image.

Conversely, when two or more bacteria colonies abut against each other, the resulting optical image is not circular in shape. Consequently, upon the mathematical insertion of the cone and the generation of the ratio between the area of the cone and the area of the "bacteria colony" outside of the cone is less than the predetermined ratio. When this occurs, the bacteria colony counter is incremented and the conical area is masked off. The remaining areas of the "bacteria colony", i.e. the abutting bacteria colonies, are then tested in a similar fashion until each bacteria colony of abutting bacteria colonies are properly counted and the counts stored in the counter.

In the case of a spiral petri dish, i.e. the specimen is dropped onto the dish while the dish is rotated, opposing segments of the petri dish are analyzed and the bacteria colonies counted. The total bacteria colony count for the entire dish is then extrapolated for the unanalyzed portions of the petri dish.

Conversely, for other bacteria specimens in which the bacteria specimen is simply applied to the petri dish, the entire area of the petri dish is analyzed in accordance with the present invention.

The device of the present invention thus not only provides a rapid, but also accurate, count of the number of bacteria colonies on a particular petri dish. Classification of bacteria colonies as a function of size is also within the scope of the invention.

BRIEF DESCRIPTION OF THE DRAWING

FIG. 2A–FIG. 2C are views illustrating the actual construction of a portion of the preferred embodiment of the present invention; and FIG. 3 is a flow chart illustrating the operation of the preferred embodiment of the present invention.

DETAILED DESCRIPTION OF A PREFERRED EMBODIMENT OF THE PRESENT INVENTION

Figure 1:
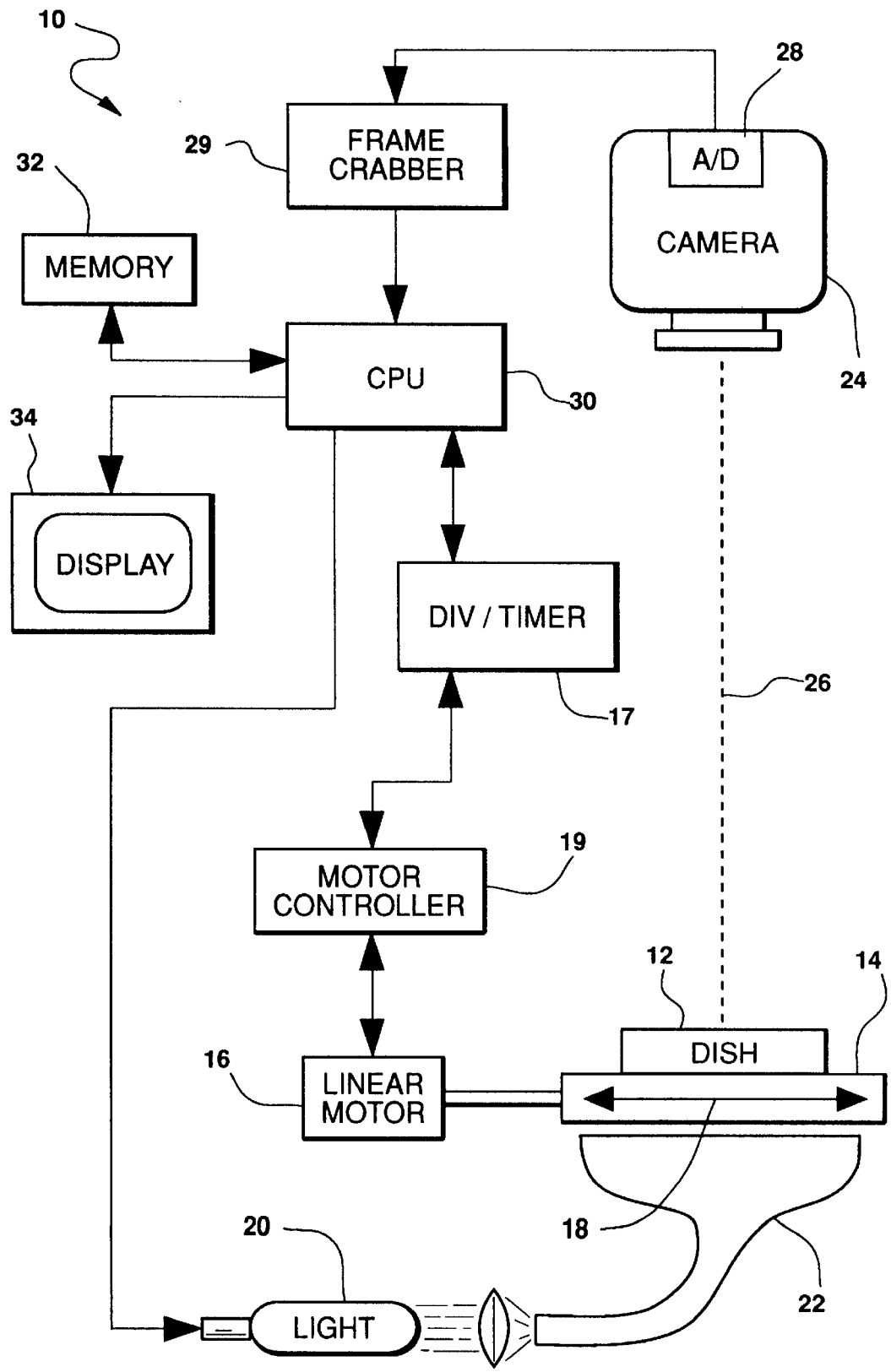
FIG. 1 is a block diagrammatic view illustrating a preferred embodiment of the present invention.
Figure 2A:
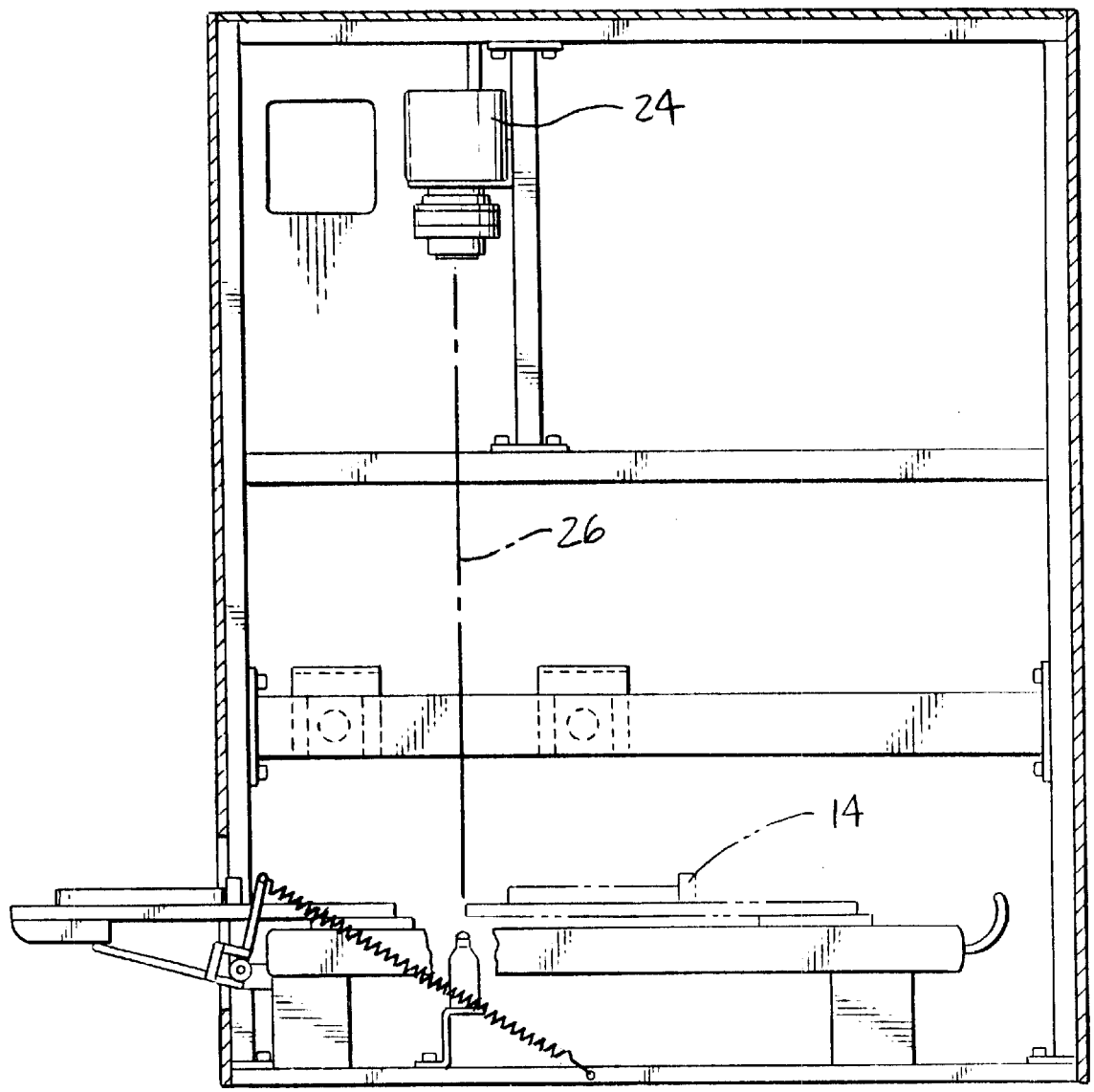

With reference first to FIG. 1, a block diagrammatic view of the bacteria colony counter and classifier 10 is there shown in which a petri dish 12 containing bacteria colonies is mounted onto a movable tray 14. A linear motor 16 (FIGS. 1 and 2a–2c) is mechanically connected to the tray 14 such that, upon actuation of the linear motor 16, the tray 14 with its attached dish 12 moves in the direction indicated by arrow 18.

A light source 20 is coupled through a fiber optic bundle 22 to a position beneath the tray 14. The tray 14, in turn, has an open bottom so that light emitted from the optical bundle 22 passes through the tray 14 and through the bottom of the dish 12.

A line scanning camera 24 is mounted above the tray 14, and thus above the dish 12 so that its line scanning image 26 scans a line along the width of the dish 12 equal to one pixel in width. The camera 24 internally converts the analog signal to a digital signal by an A/D converter 28 and the digitized signal is then coupled via a conventional image acquisition device 29 to a digital computer 30.

The digital computer 30 controls the actuation of the linear motor 16 via a divider/timer circuit 17 and motor controller 19 as well as accepting the input signal from the camera 24 so that one optical line of an optical image from the camera 24 is inputted by the computer 30 each time the tray 14 with its attached dish 12 is moved by the linear motor 16 a distance equal to one pixel width. As such, the total optical image inputted by the computer 30 corresponds to an optical image of the entire dish 12 with bacteria colonies contained therein as the dish 12 is moved under the scanning line 26. This optical image is stored in digital memory 32 as well as presented on a visual display 34.

After the image of the dish 12 with the bacteria colonies has been scanned and stored in memory 32 in the above-described fashion, the digital image is then analyzed by software contained in the memory 32 to not only differentiate, but also count and optionally classify the bacteria colonies by size.

The discrimination of an object from a background in a digitized gray level image has proven to be a long-standing problem. The present invention offers a solution to the long-standing problems of accurately defining the border regions between an object and a background, as well as segregating multiple contiguous objects. The instant invention finds particular utility in segregating bacterial colonies from the underlying growth medium.

The present invention operates to analyze an image from a gray-scale input. The gray-scale input typically being 8 bits or 256 values. However, it is appreciated that other gray-scale input such as 4 bit or 16 bit are also operative herein. An initial function of the instant invention is to dichotomize the pixels of an image into two classes, namely background and object. Thus, a segmentation routine of the instant invention dichotomizes the gray-scale image into a binary image where zero denotes background and one denotes object (or vice versa).

A selected gray-scale image is initially filtered in the instant invention. The image is filtered using a morphological filter known in the art as "closing." The size of the filter utilized is such that the largest object (or contiguous cluster of objects) encountered in the image is smaller in at least one dimension than the filter. In this way, the instant invention assures that the largest object(s) is adequately filtered and thereby assigned a binary value associated with an object.

Closing, as a filter process has two distinct steps, dilation, followed by erosion. For the purposes of describing the present invention a dilation followed by an erosion is detailed. However, it is appreciated that a functional result is obtained by reversing the sequence of the distinct steps, thereby filtering by a process known in the art as "opening." A dilation is defined as replacing a given pixel with the maximum value of any of the neighbor pixels. The group of neighboring pixels used for the dilation designates the size and shape of the structuring element of the closing filter. A structuring element is thus a list of pixels, offset from the pixel of interest. Typical structuring elements include the eight adjacent pixels about the pixel of interest in a square array, and a linear pixel array centered about the pixel of interest. A dilation is carried out in the present invention by applying the structural element sequentially to each pixel contained within the original gray-scale image. The maximum value contained within the original image data found within the structuring element of the filter is then stored in a filtered image file for the pixel of interest. As the structuring element is applied to each pixel of the image, the object areas preferentially are darkened. Following dilation, the filtered image data is updated by an erosion. An erosion is defined as the replacement of a given pixel value with the minimum value of the pixels in the structuring element. It is appreciated that the application of a structuring element to update a pixel of interest may actually also be used to update a neighbor of the pixel of interest (a member of the structuring element). By the same process as the dilation, an erosion operation replaces the pixel of interest with the minimum value of the pixels in the structuring element. Preferably, the same structuring element is applied in both the dilation and erosion operations of a given closing.

In a case where the selected gray-scale image represents bacterial colony growth on a medium, a linear structuring element is preferred. The typical rotational symmetry of bacterial colonies favors the use of such a structuring element, however, it is appreciated that two dimensional structuring elements are applicable to images in which the bacterial colonies are contiguous and, in the extremum, form fractal-like arrangements. Preferably, a linear structuring element is specified which is one pixel high and N pixels long, where N is approximately twice the diameter of the largest colony captured in the gray-scale image (in pixel units). More preferably, the pixel of interest is the pixel being updated and is located in the center of the long, thin structuring element. The effect of closing on an original gray-scale image is to preferentially darken low contrast colonies, as compared to large, dark colony regions which are relatively unaffected by the filter. A suitable structuring element has the net affect of filtering out all of the colonies (if any) from the original gray-scale image. Thus, a successful filtration yields an average region of background corresponding to the bacterial growth medium, in which all the pixels have approximately uniform values. An analysis step follows in the instant invention, in order to determine if a successful filtration has occurred.

Analysis of the image segmentation in the instant invention is performed by applying an automatic segmentation routine developed by N. Otsu, IEEE Transactions on Systems, Man and Cybernetics, Vol. SMC-9, No. 1, January, 1979; which is incorporated herein by reference. While the present invention utilizes the automatic segmentation routine of Otsu to calculate parameters such as probabilities of background and object class occurrence, mean class levels, and class variances, the present invention calculates a value not contemplated by Otsu, in order to determine the effectiveness of the filtration. Otsu teaches a method for determining the optimal segmentation threshold for an image by maximizing the dichotomy between background and object classes in gray scales. The Otsu procedure computes the zeroth (–) and the first-cumulative moments of the gray-scale histogram in order to calculate the optimal threshold. This threshold represents the maximal variance between object and background classes within the original gray-scale image. In contrast, the present invention utilizes the value of the variance between the object (bacterial colony) and background (medium) to determine the effectiveness of image filtration. For instance, a variance computed upon closing of less than 150 for a 256 value gray-scale image is considered too low for a dichotomy of classes to be present, indicating that the filtered image is uniform and possesses inconsequential segregation. Thus, the particular filter chosen operated successfully and filtered out the objects (colonies) from the background (medium). A variance below 150 is indicative of a relatively uniform filtered background. The Otsu threshold selection methodology encounters difficulties in evaluating an image with such modest variations in gray scale.

In those instances when the present invention returns a value of variance greater than 150, then the filtration is deemed not to have been successful. A variance of greater than 150 in the present invention is attributable in the case of bacterial colony images to either an excessively large mass of colonies being present in the medium (a "lawn") or alternatively, there is an excessive optical density variation within the bacterial growth medium.

Regardless of the cause, a filtered image returning a variance of greater than 150 is first inverted. Inversion constitutes changing the value of a pixel of interest to equal 255 minus the original gray-scale value of the pixel of interest. Following image inversion, the Otsu segmentation routine is reapplied. Should the value of the variance thus computed be greater than 500, then the optimal threshold value as calculated by the Otsu routine is applied. However, when the value of the variance is less than or equal to 500, the optimal threshold for image segmentation is set at the greater of: 1) the threshold value computed by Otsu or, 2) the numerical value 20 (for a 256 level image). Following the corrective thresholding operation, the present invention proceeds to separate contiguous objects.

In instances where the value of the variance is below 150 and therefore the image is well separated into background and object, the following series of steps follows in the course of the present invention. Upon confirmation of a successful filtration, the original unfiltered gray scale image is subtracted from the filtered image. The result of this subtraction is an image derived from objects (bacterial colonies) on background (medium) characterized by near zero values where only medium is present and higher values (greater than the near zero values in regions where colonies had been filtered out by closing. The value of the pixels in the regions where colonies had been filtered out, are essentially the difference in intensity values between the colony and neighboring medium values. The resulting subtracted image is analyzed a second time with the Otsu segmentation routine. A value of the variance greater than 500 is anticipated, thereby indicating satisfactory separation between objects and background. Upon obtaining a variance of greater than 500 the optimal threshold computed by Otsu is utilized to dichotomize the image. By way of example, a subtracted image derived from bacterial colonies on medium are converted to a binary image by replacing individual pixel values greater than the Otsu threshold (colonies) with ones and individual pixel values less than this threshold (medium) being replaced by zeros.

In instances where the value of the variance is less than 500, indicating an unsuitable separation, then the threshold is set at an operator determined fixed value. Typically, the fixed value supplied in such an instance is about 15. The utility of automatic filtering and segmentation is to reduce operator intervention in using the system. Instead of adjusting the system for each individual plate being processed, adjustments are only needed for the media type of the plate.

As previously described, the software routine to identify the bacteria colonies utilizes a conical fitting routine which identifies circular masses which generally correspond to bacterial colonies. In the event of abutting bacteria colonies, the resulting optical image is generally not circular in shape. In this event, the software selectively identifies the circular areas of the optical image of abutting colonies and selectively masks off each such identified colony until each and substantially every one of the abutting colonies are identified and counted.

In the case of a spiral bacterial specimen, i.e. a specimen in which the dish 12 is rotated while the bacteria specimen is dropped onto the dish, the bacteria colonies are counted in opposing sectors and then that count extrapolated for the unanalyzed area of the optical image to determine the total bacteria count for the dish 12. Conversely, in the event that the bacteria is applied without spinning to the petri dish, the entire optical image of the dish with its contained bacteria colonies.

With reference now to FIG. 3, a flow chart illustrating the operation of the preferred embodiment of the present invention is there shown. At step 100, the petri dish 12 is scanned by the line scan camera 24 in synchronism with the movement of the tray 14 across the optical field of vision for the camera 24 until a complete image of the dish 12, and thus of the bacteria colonies, is obtained. Step 100 then exits to step 102 where the image is normalized in any conventional fashion.

Step 102 then branches to step 104 which determines, based upon user input, if a spiral or whole count of the dish is desired. In the event of a spiral count, step 104 branches to step 106 which sets the sector count to one and then branches to step 108.

At step 108, a sector mass is applied is applied to the optical image so that only the bacteria colonies within that particular sector remain. Step 108 then branches to step 110 which segments the image. Step 110 then branches to step 112 which determines if it is necessary to separate the colonies, i.e. colonies that are in abutment with each other. If so, step 112 branches to step 114 and proceeds to count the bacteria colonies with separation in utilizing the conical mass procedure previously described. Otherwise, step 112 branches to step 116 which counts the colonies without separation.

After counting the colonies of either step 114 or 116, both steps 114 and 116 branch to step 118 which determine if enough colonies have been counted by comparing the colony count with a predetermined constant. For example, a colony count which is too low will result in an inaccurate colony count for the entire petri dish when the sector count is extrapolated to apply to the entire dish. Conversely, when the colony count is relatively high, extrapolation of the colony count to the entire petri dish can be utilized with acceptable accuracy.

If insufficient colonies have been counted at step 118, step 118 branches to step 120 which increments the sector count and then reiterates steps 108–118 until sufficient colonies have been counted. In that event, step 118 branches to step 120 which sums the results of the count of the colonies after extrapolation throughout the entire petri dish and then returns this result at step 122.

On the other hand, if a whole count for the petri dish, as opposed to a spiral count, is desired, step 104 instead branches to step 124 which applies a mask to the entire plate and then to step 126 which segments the image. Step 126 then branches to step 128.

Step 128 determines if separation of the colonies is required and, if so, branches to step 130 which counts the colonies with the separation method previously described. Otherwise, step 128 branches to step 132 which counts the bacteria colonies without separation and then to step 122 which returns the result of the bacteria colony count.

Having described my invention many modifications thereto will become apparent to those skilled in the art to which it pertains without deviation from the spirit of the invention as defined by the scope of the appended claims.

We claim:

1. A system for automatically counting bacteria colonies in a dish containing a translucent bacteria supporting media comprising:

a line scanning camera having an output signal representative of light intensity along a predetermined scan line, said scan line having a predetermined thickness, a conveyor which moves the dish along a predetermined path of movement substantially perpendicular to and intersecting said scan line, a light source optically coupled with the dish during movement along said path of movement, a processor having digital memory;

said processor inputting said camera output signal into memory in sychronism with the movement of the dish corresponding to said scan line thickness, said processing means storing said camera output signal in said digital memory to thereby form a complete image of the dish in said digital memory, means for analyzing said complete image stored in said digital memory and for differentiating bacteria colonies from the bacteria supporting media, and means for counting said bacteria colonies.

2. The invention as defined in claim 1 wherein said scan line thickness corresponds to one pixel.

3. The invention as defined in claim 1 wherein said light source is optically coupled by a fiber optic bundle having one end exposed to said light source and a second end facing the dish on the side opposite from the line scan camera.

4. The invention as defined in claim 1 wherein said processor comprises a microprocessor.

5. The invention as defined in claim 1 wherein said conveyor comprise a slidable tray and a linear motor for moving said tray.

6. The invention as defined in claim 1 wherein said processor is programmed to differentiate between abutting bacteria colonies which form a bacteria cluster.

7. The invention as defined in claim 6 wherein said processor differentiates between abutting bacteria colonies by mathematically inserting a cone into the bacteria cluster until an outer edge portion of the cone corresponds to an outer edge portion of the bacteria cluster, and then masking the area within the cone.

* * * * *